United States Patent [19]
Hansen et al.

[11] Patent Number: 4,908,437
[45] Date of Patent: Mar. 13, 1990

[54] THIEN-2-ONE COMPOUNDS WITH AN ALKYLIDENE OR IMINO GROUP IN THE 5-POSITION OF THE RING

[75] Inventors: Guenter Hansen, Ludwigshafen; Johannes P. Dix, Neuhofen; Helmut Reichelt, Niederkirchen; Masahiro Hayashi, Ludwigshafen, all of Fed. Rep. of Germany

[73] Assignee: BASF Aktiengesellschaft, Ludwigshafen, Fed. Rep. of Germany

[21] Appl. No.: 195,668

[22] Filed: May 17, 1988

[30] Foreign Application Priority Data

May 19, 1987 [DE] Fed. Rep. of Germany ....... 3716656

[51] Int. Cl.$^4$ .................... C09B 29/09; C07D 333/32; C07D 333/36; C07D 333/38
[52] U.S. Cl. ........................ 534/738; 8/574; 8/575; 8/662; 534/751; 534/753; 534/775; 534/887; 549/59; 549/61; 549/62; 549/63
[58] Field of Search ............... 534/775, 751, 753, 738; 549/59, 61, 62, 63; 8/574, 575, 662

[56] References Cited

U.S. PATENT DOCUMENTS

| | | |
|---|---|---|
| 2,500,822 | 3/1950 | Hartough et al. ................. 549/62 X |
| 2,685,509 | 8/1954 | Doyle et al. ...................... 549/61 X |
| 4,092,329 | 5/1978 | Jotterand ............................. 549/61 |
| 4,111,956 | 9/1978 | Baird et al. .......................... 549/61 |
| 4,214,091 | 7/1980 | Oishi et al. .......................... 549/62 |
| 4,239,894 | 12/1980 | Seybold et al. ................. 534/728 X |

FOREIGN PATENT DOCUMENTS

| | | |
|---|---|---|
| 2732221 | 1/1967 | Fed. Rep. of Germany ...... 534/728 |
| 0113233 | 8/1962 | German Democratic Rep. .................... 534/728 |
| 60-166345 | 8/1985 | Japan ................................. 534/753 |
| 60-190776 | 9/1985 | Japan ................................. 549/61 |

OTHER PUBLICATIONS

Dyes and Pigments, vol. 1, pp. 3–15, (1980), "Preparing of Some New Red Fluorescent 4-Cyanocoumarin Dyes", (Moeckli).
Journal Prakt Chem., vol. 317, pp. 861–866, (1975), "Synthese und Reaktionen von 2-hydroxy-3-cyan-thiophenen", (Gewald et al).
Dissertation, M. Hentschel, Technischen Universitat Dresden, Jan. 28, 1975.

Primary Examiner—Floyd D. Higel
Attorney, Agent, or Firm—Oblon, Spivak, McClelland, Maier & Neustadt

[57] ABSTRACT

The invention relates to novel thienone compounds useful in dyeing fibers, of the formula:

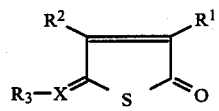

where
$R^1$ is cyano, $C_1$–$C_4$-alkoxycarbonyl, carbamoyl or $C_1$–$C_4$-monoalkylcarbamoyl or -dialkylcarbamoyl,
$R^2$ is hydrogen, $C_1$–$C_8$-alkyl, substituted or unsubstituted phenyl, furyl, thienyl or halogen,
X is nitrogen or $CR^4$ where $R^4$ is hydrogen, $C_1$–$C_4$-alkyl, $C_1$–$C_4$-alkoxycarbonyl, cyano or substituted or unsubstituted phenyl, and
$R^3$ is an aniline, thiazole, indole, styrol or isoindole radical, with the proviso that if $R^1$ is cyano, X is CH and $R^3$ is 4-dimethylaminophenyl or styryl, then $R^2$ is not methyl or phenyl and that if $R^1$ is cyano, X is CH and $R^3$ is phenyl or 4-methoxyphenyl, then $R^2$ is not phenyl.

4 Claims, No Drawings

THIEN-2-ONE COMPOUNDS WITH AN ALKYLIDENE OR IMINO GROUP IN THE 5-POSITION OF THE RING

The present invention provides novel thien-2-one compounds which have an alkylidene or imino group in the 5 position on the ring and a method of using same for dyeing fibers.

German Pat. No. 2,732,221 discloses dyes based on 1,3-thiazole derivatives which have an alkylidene group in the 2 position on the ring and an alkylidene or imino group in the 5 position on the ring.

We have now found a thienone compound of the formula I

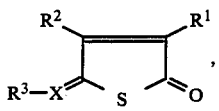

where $R^1$ is cyano, $C_1-C_4$-alkoxycarbonyl, carbamoyl or $C_1-C_4$-monoalkylcarbamoyl or -dialkylcarbamoyl, $R^2$ is hydrogen, $C_1-C_8$-alkyl, substituted or unsubstituted phenyl, furyl, thienyl or halogen, X is nitrogen or $CR^4$ where $R^4$ is hydrogen, $C_1-C_4$-alkyl, $C_1-C_4$-alkoxycarbonyl, cyano or substituted or unsubstituted phenyl, and $R^3$ is a radical of the formula

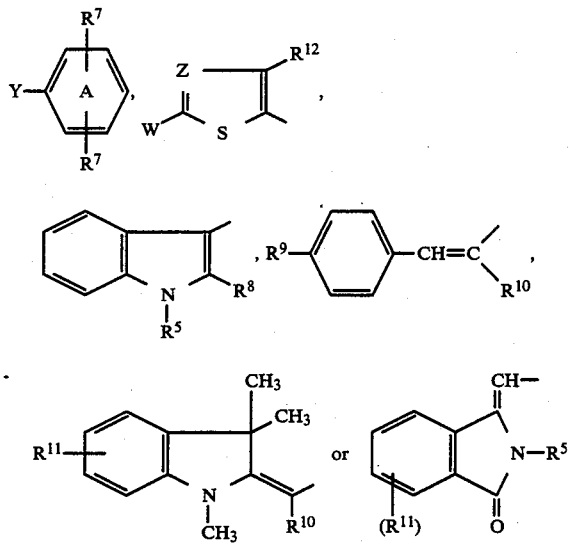

where the ring A may be benzofused,

Y is $NR^5R^6$ or $OR^8$ where $R^5$ and $R^6$ are identical or different and each is independently of the other hydrogen, $C_1-C_8$-alkyl which is unsubstituted or substituted by hydroxyl, chlorine, cyano, $C_1-C_4$-alkoxy, $C_1-C_4$-alkanoyloxy, $C_1-C_4$-alkoxycarbonyloxy or phenyl, allyl, $C_5-C_7$-cycloalkyl or phenyl or together with the nitrogen atom joining them are a 5- or 6-membered saturated heterocyclic ring and $R^8$ is $C_1-C_4$-alkyl or phenyl, the $R^7$s are independently of one another hydrogen, chlorine, bromine, hydroxyl, $C_1-C_4$-alkyl, $C_1-C_4$-alkoxy, unsubstituted or chlorine-, $C_1-C_4$-alkoxy- or phenoxy-substituted $C_1-C_4$-alkanoylamino, benzoylamino, $C_1-C_4$-mono- or -dialkylaminosulfonylamino, $C_1-C_4$-alkanoyloxy or phenylsulfonyloxy, $R^9$ is hydrogen, $C_1-C_4$-dialkylamino or $C_1-C_4$-alkoxy, $R^{10}$ is hydrogen or cyano, $R^{11}$ is hydrogen, chlorine, bromine or $C_1-C_4$-alkyl, $R^{12}$ is hydrogen, chlorine, bromine, $C_1-C_8$-alkyl, substituted or unsubstituted phenyl or thienyl, W is $NR^5R^6$ or

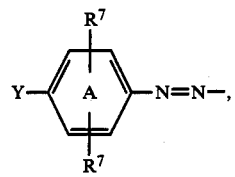

where $R^5$, $R^6$, $R^7$, Y and the ring A are each as defined above,

Z is nitrogen or $CR^1$ where $R^1$ is as defined above, and n is 1, 2, 3 or 4, with the proviso that if $R^1$ is cyano, X is CH and $R^3$ is 4-dimethylaminophenyl or styryl, then $R^2$ is not methyl or phenyl and that if $R^1$ is cyano, X is CH and $R^3$ is phenyl or 4-methoxyphenyl, then $R^2$ is not phenyl.

3-Cyanothien-2-ones which are substituted by phenyl in ring position 4 and by benzylidene, 4-methoxybenzylidene, 4-dimethylaminobenzylidene or 3-phenylprop-2-enylidene in ring position 5 or by methyl in ring position 4 and by 4-dimethylaminobenzylidene or 3-phenylprop-2-enylidene in ring position 5 are known and described in J. Prakt. Chem. 317 (1975), 867 and also in the dissertation by M. Hentschel, Technical University of Dresden, Jan. 28, 1975.

All the alkyl groups appearing in the abovementioned radicals of the formula I can be not only straight-chain but also branched. Where the phenyl radicals appearing in the formula I are substituted, suitable substitutents for each instance are for example $C_1-C_4$-alkyl, $C_1-C_4$-alkoxy, chlorine, bromine and nitro.

In the formula I, $R^1$ and $R^4$ are each for example methoxycarbonyl, ethoxycarbonyl, propoxycarbonyl, isopropoxycarbonyl, butoxycarbonyl or sec-butoxycarbonyl.

$R^1$ is further for example methylcarbamoyl, ethylcarbamoyl, propylcarbamoyl, isopropylcarbamoyl, butylcarbamoyl, dimethylcarbamoyl, diethylcarbamoyl, dipropylcarbamoyl, diisopropylcarbamoyl, dibutylcarbamoyl or N-methyl-N-ethylcarbamoyl.

$R^2$, $R^5$, $R^6$, $R^7$, $R^8$, $R^{11}$ and $R^{12}$ are each for example methyl, ethyl, propyl, isopropyl, butyl, isobutyl, sec-butyl or tert-butyl.

$R^2$, $R^5$, $R^6$ and $R^{12}$ are each further for example pentyl, isopentyl, sec-pentyl, tert-pentyl, hexyl, 2-methylpentyl, heptyl, 2-methylhexyl, octyl or 2-ethylhexyl.

$R^2$ is further for example fluorine, chlorine or bromine.

$R^5$ and $R^6$ are each further for example 2-hydroxyethyl, 2-chloroethyl, 2-cyanoethyl, 2-methoxyethyl, 2-ethoxyethyl, 2-propoxyethyl, 2-butoxyethyl, 2-formyloxyethyl, 2-acetyloxyethyl, 2-propionyloxyethyl, 2-butyryloxyethyl, 2-methoxycarbonyloxyethyl, 2-ethoxycarbonyloxyethyl, 2-propoxycarbonyloxyethyl, 2-butoxycarbonyl-oxyethyl, 2-methoxypropyl, 3-methoxypropyl, benzyl, 1- or 2-phenylethyl, phenyl, cyclopentyl, cyclohexyl or cycloheptyl.

$R^5$ and $R^6$ are further with the nitrogen atom joining them for example pyrrolidino, piperidino, morpholino, piperazino or N-($C_1$-$C_4$-alkyl)piperazino, such as N-methylpiperazino or N-ethylpiperazino.

$R^7$ and $R^9$ are each further for example methoxy, ethoxy, propoxy, isopropoxy, butoxy, isobutoxy or sec-butoxy.

$R^7$ is further for example formylamino, acetylamino, propionylamino, butyrylamino, isobutyrylamino, chloroacetylamino, methoxyacetylamino, ethoxyacetylamino, phenoxyacetylamino, 3-chloropropionylamino, 3- or 4-methoxybutyrylamino, methyl- or ethylaminosulfonylamino, dimethylaminosulfonylamino, diethylaminosulfonylamino, formyloxy, acetyloxy, propionyloxy, butyryloxy or isobutyryloxy.

$R^9$ is further for example methylamino, ethylamino, propylamino, isopropylamino, butylamino, dimethylamino, diethylamino, dipropylamino, diisopropylamino or N-methyl-N-ethylamino.

$R^2$, $R^4$ and $R^{12}$ are each further for example 2- or 4-methylphenyl, 4-ethylphenyl, 4-isopropylphenyl, 2,4-dimethylphenyl, 2- or 4-methoxyphenyl, 4-ethoxyphenyl, 2,4-dimethoxyphenyl, 2- or 4-chlorophenyl, 2- or 4-bromophenyl, 2,6-dichlorophenyl or 3-nitrophenyl.

$R^3$ is inter alia for example of the formula

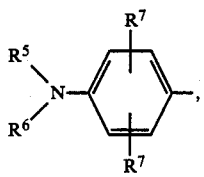

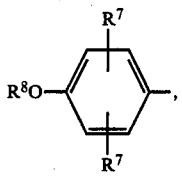

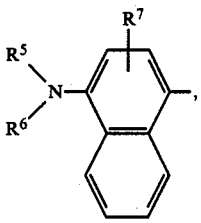

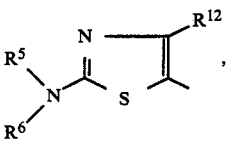

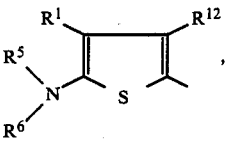

-continued

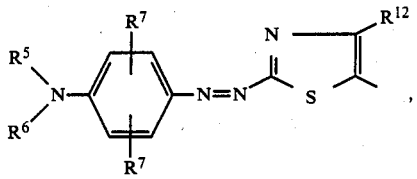

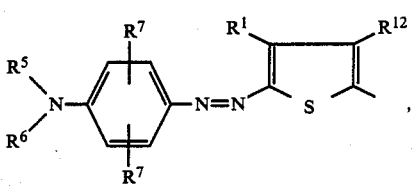

or 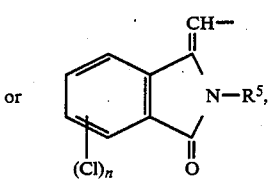

where $R^1$, $R^5$, $R^6$, $R^7$, $R^8$, $R^{12}$ and n are each as defined above.

Preference is given to those thienone compounds of the formula I where $R^1$ is cyano or carbamoyl, $R^2$ is $C_1$-$C_4$-alkyl, unsubstituted or methyl-, ethyl-, methoxy-, ethoxy-, chlorine- or bromine-substituted phenyl or thienyl, X is nitrogen or $CR^4$ where $R^4$ is hydrogen or cyano and $R^3$ is a radical of the formula

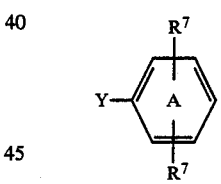

where Y, $R^7$ and the ring A are each as defined above.

Preference is given in particular to thienone compounds of the formula I where $R^1$ is cyano, $R^2$ is methyl, unsubstituted or methoxy-substituted phenyl or thienyl, X is nitrogen or $CR^4$ where $R^4$ is hydrogen or cyano and, $R^3$ is a radical of the formula

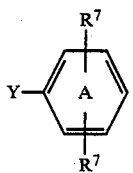

where the ring A is not benzofused and Y and $R^7$ are each as defined above.

To prepare a compound of the formula I, for example a 2-hydroxythiophene of the formula II

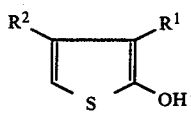 (II)

where $R^1$ and $R^2$ are each as defined above, is condensed with a compound of the formula III

 (III)

where $R^3$ and X have the abovementioned meanings [except X=C(CN)]. If a compound of the formula III is an aldehyde or ketone, it can be advantageous in some cases to use it in acetal form.

The condensation is advantageously carried out in an inert solvent at from 20° to 160° C., preferably at from 20° to 100° C. Suitable solvents are for example methanol, ethanol, propanol, isopropanol, butanol, isobutanol, methylglycol, dioxane, acetone, acetonitrile, N,N-dimethylformamide, N-methylpyrrolidone, toluene, xylene, chlorobenzene and nitrobenzene. Preference is given to working in alcohols, for example in propanol.

The condensation can also be carried out in the presence of acid or basic catalysts. The water formed in the course of the reaction can, if a suitable solvent is used, for example toluene, be removed from the reaction mixture azeotropically. However, it is also possible to carry out the reaction in the presence of water.

Suitable acid catalysts are for example mineral acids, such as hydrochloric acid or sulfuric acid, carboxylic acids, such as formic acid, acetic acid or trichloroacetic acid, phosphorus oxychloride, phosphorus pentachloride, phosphorus trichloride and thionyl chloride.

Suitable basic catalysts are for example ammonium acetate and amines, such as piperidine, pyrrolidine, pyridine, triethylamine and triethanolamine.

To prepare those compounds of the formula I where X is C(CN), it is possible to react those compounds of the formula I where X is CH with metal cyanides, such as sodium cyanide or potassium cyanide, and in a subsequent reaction to reoxidize with suitable oxidizing agents, for example bromine, $K_3[Fe(CN)_6]$, $Pb(OAc)_4$ or $FeCl_3 \times 6H_2O$. This method of cyanation is described in Dyes and Pigments 1 (1980), 3 for coumarin derivatives.

Some compounds of the formula II are known from the abovementioned references. In addition, DD-A-113,233 describes a process for preparing 2-hydroxy-3-cyanothiophenes whose ring position 5 is unsubstituted (for example 2-hydroxy-3-cyano-4-phenylthiophene).

Further details of the preparation can be found in the Examples.

We have further found that the thienone compounds of the formula Ia

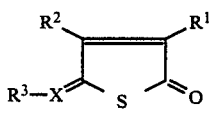 (Ia)

where
$R^1$ is cyano, $C_1$-$C_4$-alkoxycarbonyl, carbamoyl or $C_1$-$C_4$-mono- or -dialkylcarbamoyl,
$R^2$ is hydrogen, $C_1$-$C_8$-alkyl, substituted or unsubstituted phenyl, furyl, thienyl or halogen, X is nitrogen or $CR^4$ where $R^4$ is hydrogen, $C_1$-$C_4$-alkyl, $C_1$-$C_4$-alkoxycarbonyl, cyano or substituted or unsubstituted phenyl, and
$R^3$ is a radical of the formula

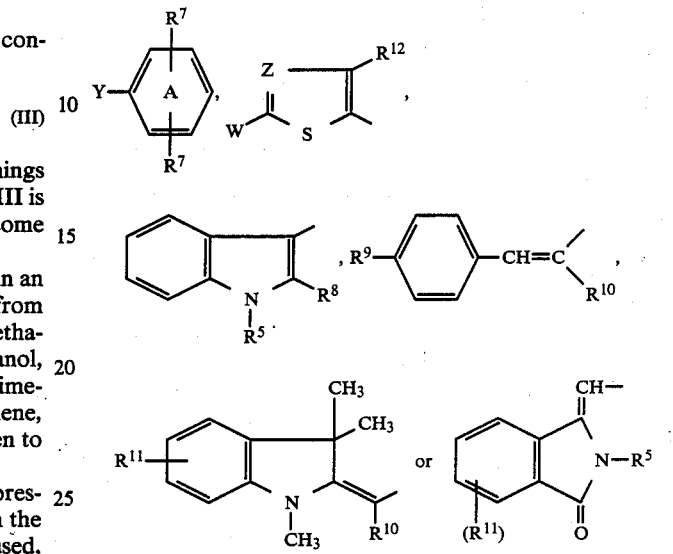

where the ring A may be benzofused,
Y is $NR^5R^6$ or $OR^8$ where $R^5$ and $R^6$ are identical or different and each is independently of the other hydrogen, $C_1$-$C_8$-alkyl which is unsubstituted or substituted by hydroxyl, chlorine, cyano, $C_1$-$C_4$-alkoxy, $C_1$-$C_4$-alkanoyloxy, $C_1$-$C_4$-alkoxycarbonyloxy or phenyl, allyl, $C_5$-$C_7$-cycloalkyl or phenyl or together with the nitrogen atom joining them are a 5- or 6-membered saturated heterocyclic ring and $R^8$ is $C_1$-$C_4$-alkyl or phenyl,
the $R^7$s are independently of one another hydrogen, chlorine, bromine, hydroxyl, $C_1$-$C_4$-alkyl, $C_1$-$C_4$-alkoxy, unsubstituted or chlorine-, $C_1$-$C_4$-alkoxy-, or phenoxy-substituted $C_1$-$C_4$-alkanoylamino benzoylamino, $C_1$-$C_4$-mono- or dialkylaminosulfonylamino, $C_1$-$C_4$-alkanoyloxy or phenylsulfonyloxy,
$R^9$ is hydrogen, $C_1$-$C_4$-dialkylamino or $C_1$-$C_4$-alkoxy,
$R^{10}$ is hydrogen or cyano,
$R^{11}$ is hydrogen, chlorine, bromine or $C_1$-$C_4$-alkyl,
$R^{12}$ is hydrogen, chlorine, bromine, $C_1$-$C_8$-alkyl, substituted or unsubstituted phenyl or thienyl,
W is $NR^5R^6$ or

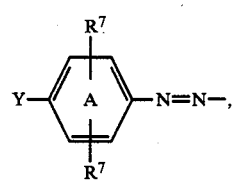

where $R^5$, $R^6$, $R^7$, Y and the ring A are each as defined above,
Z is nitrogen or $CR^1$ where $R^1$ is as defined above, and
n is 1, 2, 3 or 4,
are suitable for use as dyes. They are suitable in particular for dyeing fibers, such as polyesters, polyamides, cellulose esters or blend fabrics of polyesters and cellulose fibers.

Brilliant dyeings are obtained in yellow to greenish blue shades having good fastness properties, in particular on polyesters. In addition, the dyes show high tinctorial strength.

The Examples which follow serve to illustrate the invention in more detail.

(A) Preparation of 2-hydroxythiophenes unsubstituted in ring position 5

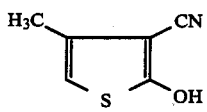

A solution of 3.9 g of sodium in 100 ml of ethanol was added dropwise in the course of 1 hour to 18.5 g of 2-amino-3-ethoxycarbonyl-4-methylthiophene in 200 ml of toluene at from 80° to 85° C. under nitrogen. 200 ml of an ethanol/toluene mixture were then distilled out of the reaction mixture at from 85° to 100° C. The precipitate which remained was filtered off at room temperature with suction, washed with a little toluene and dissolved in 250 ml of water. The solution was brought to a pH of 1 with concentrated hydrochloric acid, 100 ml of methylene chloride were added, and the organic phase was separated off and concentrated.

Yield: 11.0 g of initially oil, later crystalline 2-hydroxy-3-cyano-4-methylthiophene (79% of theory).

Melting point: 52°–53° C. (petroleum ether).

Table 1 gives 3-cyano-2-hydroxythiophenes of the formula

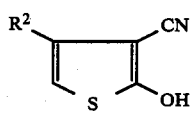

obtained in a similar manner.

TABLE 1

| Example | R² |
|---|---|
| 2 | —⟨C₆H₄⟩—OCH₃ |
| 3 | —⟨C₆H₄⟩—CH₃ |
| 4 | —⟨C₆H₄⟩—Cl |
| 5 | —⟨C₆H₃⟩(OCH₃)(OCH₃) |

TABLE 1-continued

| Example | R² |
|---|---|
| 6 | (2-thienyl) |

EXAMPLE 7

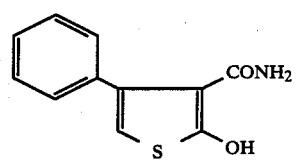

2.01 g of 3-cyano-2-hydroxy-4-phenylthiophene were added at 90° C. with stirring to 50 g of polyphosphoric acid. The reaction mixture was stirred at that temperature for 4 hours. After cooling down, 50 g of ice were added, the mixture was stirred for one hour, and the precipitate was filtered off with suction and thoroughly washed with water to give 1.6 g (73% of theory) of 3-carbamoyl-2-hydroxy-4-phenylthiophene having a melting point of 108°–110° C.

Table 2 gives 3-carbamoyl-2-hydroxythiophenes of the formula

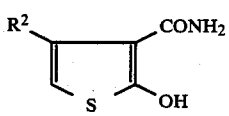

obtained in a similar manner.

TABLE 2

| Example | R² |
|---|---|
| 8 | —⟨C₆H₄⟩—OCH₃ |
| 9 | —⟨C₆H₄⟩—CH₃ |
| 10 | —CH₃ |

(B) Preparation of thienones according to the invention

EXAMPLE 11

2.01 g of 3-cyano-2-hydroxy-4-phenylthiophene and 3.20 g of 3-methoxy-4-nitroso-N,N-dihexylaniline were stirred at 25° C. in 60 ml of n-propanol for 12 hours. This was followed by discharging onto 500 ml of water, stirring for 15 minutes, filtering off with suction and drying to give 4.9 g of a dye (97% of theory) which dyes polyester fibers in a brilliant neutral blue shade.

$\lambda_{max}$ (CH₂Cl₂): 602 nm.

EXAMPLE 12

2.01 g of 3-cyano-2-hydroxy-4-phenylthiophene and 2.31 g of 4-nitroso-N-butyl-N-(2-cyanoethyl)aniline were stirred at 25° C. in 50 ml of n-propanol for 10 hours. After 100 ml of water had been added, the dye was filtered off with suction, washed with water and dried.

Yield: 4.00 g (97% of theory), melting point 164°-166° C. (propanol), $\lambda_{max}$ (CH$_2$Cl$_2$): 556 nm. The dye dyes polyester in violet shades.

EXAMPLE 13

1.74 g of 3-cyano-2-hydroxy-4-methylthiophene and 1.39 g of 4-N,N-diethylaminobenzaldehyde were stirred at 20° C. in 40 ml of n-propanol for 14 hours. The precipitate was filtered off with suction and washed with a little propanol. 2.85 g were obtained of a dye (96% of theory) which dyes polyester fiber material in brilliant yellowish red shades.

Melting point: 205°-207° C. (propanol), $\lambda_{max}$ (CH$_2$Cl$_2$): 521 nm.

Table 3 gives dyes obtained in a similar manner in terms of the respective two starting components.

TABLE 3

Thiophene component structure (common to all rows):

R$^2$ and R$^1$ on thiophene ring with S and OH; R$^1$ = CN, R$^2$ = C$_6$H$_5$ in all examples below.

| Example | R$^3$—X=O | Hue on polyester | $\lambda_{max}$ [nm] (CH$_2$Cl$_2$) |
|---|---|---|---|
| 14 | 4-C$_2$H$_5$O-C$_6$H$_4$-CHO | yellow | 430 |
| 15 | 3,4-(CH$_3$O)$_2$-C$_6$H$_3$-CHO | yellow | 445 |
| 16 | 4-(H$_5$C$_2$)$_2$N-2-NHCOCH$_3$-C$_6$H$_3$-NO | blue | 612 |
| 17 | N-(H$_2$C=CH-CH$_2$)-N-(NC-H$_4$C$_2$)-amino on benzene with OCH$_3$, NO, NHCOCH$_3$ substituents | blue | — |
| 18 | 4-(H$_5$C$_2$)$_2$N-C$_6$H$_4$-NO | blue | 589 |
| 19 | 4-(H$_5$C$_2$)$_2$N-3-OCH$_3$-C$_6$H$_3$-NO | blue | 597 |
| 20 | 4-(H$_5$C$_2$)$_2$N-C$_6$H$_4$-CHO | red | — |
| 21 | 4-(H$_5$C$_2$)$_2$N-2-OH-C$_6$H$_3$-CHO | red | — |

TABLE 3-continued

| Example | R³—X=O | R²-[thiophene with R¹, OH] | Hue on polyester | λmax [nm] (CH₂Cl₂) |
|---|---|---|---|---|
| 22 | 1,3,3-trimethyl-2-(formylmethylene)indoline (N-CH₃, 3,3-(CH₃)₂, =CH—CHO) | R¹=CN, R²=C₆H₅, OH on thiophene | reddish violet | 552 |
| 23 | (H₅C₂)₂N—C(=N—)—S—; vinyl bearing thiophene and CHO | R¹=CN, R²=C₆H₅, OH | violet | 572 |
| 24 | (CH₃)₂N—C₆H₄—CH=CH—CHO | R¹=CN, R²=C₆H₅, OH | blue | 578 |
| 25 | (H₅C₂)₂N—C₆H₃(OCOCH₃)—N=O | R¹=CN, R²=C₆H₅, OH | reddish blue |  |
| 26 | (H₅C₂)₂N—C₆H₃(OSO₂C₆H₅)—NO | R¹=CN, R²=C₆H₅, OH | reddish blue |  |
| 27 | (H₅C₂)₂N—C₆H₃(OSO₂C₆H₅)—CHO | R¹=CN, R²=C₆H₅, OH | red |  |
| 28 | H₅C₂(NCH₄C₂)N—C₆H₄—CHO | R¹=CN, R²=C₆H₅, OH | scarlet |  |
| 29 | (C₃H₇)₂N—C₆H₄—CHO | R¹=CN, R²=C₆H₅, OH | red |  |
| 30 | H₉C₄(NCH₄C₂)N—C₆H₃(OCH₃)—CHO | R¹=CN, R²=C₆H₅, OH | red |  |
| 31 | H₉C₄(NCH₄C₂)N—C₆H₃(OCH₃)—NO | R¹=CN, R²=C₆H₅, OH | reddish blue |  |

TABLE 3-continued

| Example | R³—X=O | (thiophene structure with R¹, R² and OH) | Hue on polyester | λmax [nm] (CH₂Cl₂) |
|---|---|---|---|---|
| 32 | 4-(N-ethyl-N-butyl)amino-2-nitroso-3-(acetylamino)benzene | R¹=CN, R²=C₆H₅ | blue | |
| 33 | 4-(N-ethyl-N-phenyl)amino-nitrosobenzene | R¹=CN, R²=C₆H₅ | blue | |
| 34 | 4-(N-methyl-N-phenyl)amino-1-nitrosonaphthalene | R¹=CN, R²=C₆H₅ | blue | 576 |
| 35 | 4-(di-n-butylamino)-2-nitroso-3-(propionylamino)benzene | R¹=CN, R²=4-CH₃O-C₆H₄ | greenish blue | |
| 36 | 4-(N-ethyl-N-butyl)amino-2-nitroso-3-(acetylamino)benzene | R¹=CN, R²=4-CH₃O-C₆H₄ | blue | |
| 37 | 4-(N-ethyl-N-butyl)amino-3-methoxy-nitrosobenzene | R¹=CN, R²=4-CH₃O-C₆H₄ | blue | |
| 38 | 4-(di-n-butylamino)-3-methoxy-nitrosobenzene | R¹=CN, R²=4-CH₃O-C₆H₄ | blue | |
| 39 | 4-(N-ethyl-N-butyl)amino-benzaldehyde | R¹=CN, R²=4-CH₃O-C₆H₄ | red | |
| 40 | 4-methoxybenzaldehyde | R¹=CN, R²=4-CH₃O-C₆H₄ | yellow | |

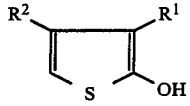
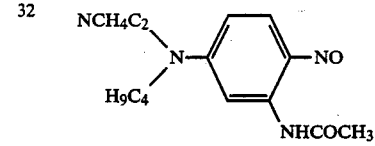
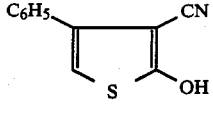
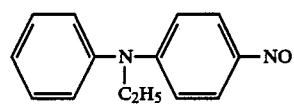
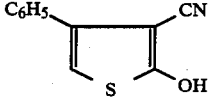
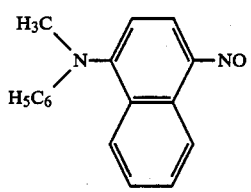
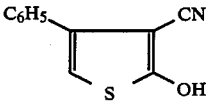
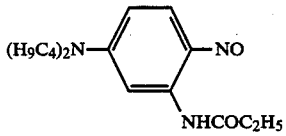
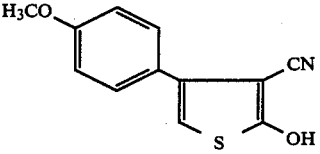
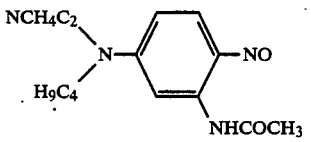
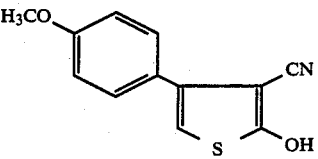
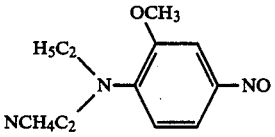
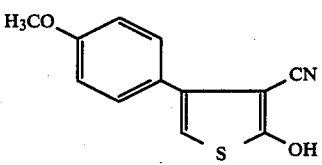
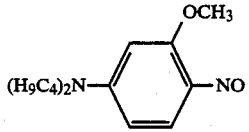
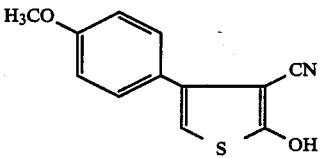
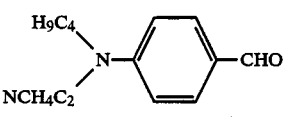
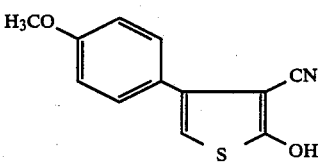
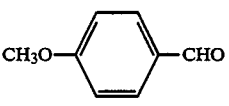
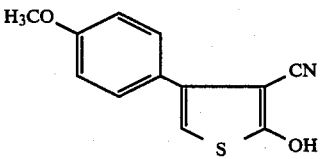

TABLE 3-continued

| Example | R³—X=O | (structure with R², R¹, OH, S) | Hue on polyester | λmax [nm] (CH₂Cl₂) |
|---|---|---|---|---|
| 41 | (H₅C₂)₂N—C₆H₃(NO)(NHCOCH₃) | bithiophene-CN-OH | greenish blue | |
| 42 | (H₁₃C₆)₂N—C₆H₃(OCH₃)(NO) | bithiophene-CN-OH | greenish blue | |
| 43 | (H₅C₂)(NC₄H₂)N—C₆H₃(NO)(OCH₃) | bithiophene-CN-OH | blue | |
| 44 | (H₅C₂)(NC₄H₂)N—C₆H₄—CHO | bithiophene-CN-OH | red | |
| 45 | (NC₄H₂)(H₅C₂)N—C₆H₃(NO)(CH₃) | bithiophene-CN-OH | blue | |
| 46 | CH₃O—C₆H₄—CHO | bithiophene-CN-OH | yellow | |
| 47 | (H₅C₂)₂N—C₆H₄—CHO | bithiophene-CN-OH | red | |
| 48 | (H₁₃C₆)₂N—C₆H₃(CHO)(CH₃) | bithiophene-CN-OH | red | |
| 49 | (H₅C₂)₂N—C(=N)—S—C(Cl)=C(CHO) | bithiophene-CN-OH | red | |
| 50 | (H₅C₂)₂N—C₆H₄—CHO | C₆H₅-thiophene-CONH₂-OH | red | |

TABLE 3-continued

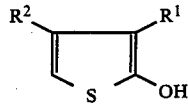

| Example | R³—X=O | (structure with R², R¹, S, OH) | Hue on polyester | λmax [nm] (CH₂Cl₂) |
|---------|--------|-------------------------------|------------------|---------------------|
| 51 | (H₅C₂)₂N—⬡—NO, NHCOC₂H₅ | C₆H₅, CONH₂, S, OH | blue | |
| 52 | C₆H₁₃O—⬡—CHO | C₆H₅, CN, S, OH | yellow | 431 |
| 53 | C₃H₇—⬡—CHO | C₆H₅, CN, S, OH | yellow | 431 |
| 54 | C₄H₅, NCC₂H₄, N—⬡—NO | (thienyl), CN, S, OH | blue | 577 |

EXAMPLE 55

1.66 g of the dye of Example 29 in 50 ml of N,N-dimethylformamide were admixed with 0.5 g of KCN and the mixture was stirred at room temperature for 1 hour. After the addition of 1.35 g of $FeCl_3 \times 6H_2O$, stirring was continued for a further 8 hours. The reaction mixture was poured onto 150 ml of ice-water, and the precipitate was filtered off and washed with water. 1.7 g (95% of theory) were obtained of the dye of the formula

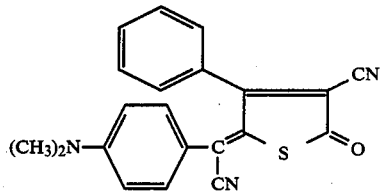

which dyes polyester in blue shades ($\lambda_{max}$ ($CH_2Cl_2$): 599).

Table 4 gives dyes of the formula

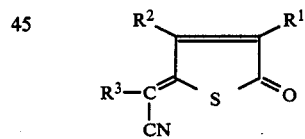

obtained in a similar manner.

TABLE 4

| Example | R³ | R² | R¹ | Hue on polyester |
|---------|----|----|----|-------------------|
| 56 | —⬡—N(C₂H₅) | C₆H₅ | CN | blue |
| 57 | (1,3,3-trimethylindol-2-ylidene-CH—) | C₆H₅ | CN | blue |

TABLE 4-continued

| Example | R³ | R² | R¹ | Hue on polyester |
|---|---|---|---|---|
| 58 | 4-methyl-2-methoxyphenyl, N(C₂H₄CN)(C₄H₉) | C₆H₅ | CN | blue |
| 59 | 4-methylphenyl-N(C₄H₉)₂ | 4-H₃CO-phenyl | CN | blue |
| 60 | 4-methyl-2-methoxyphenyl, N(C₆H₁₃)₂ | 4-H₃CO-phenyl | CN | blue |
| 61 | 4-methyl-3-methylphenyl-N(C₂H₅)₂ | 2-thienyl | CN | blue |
| 62 | 4-methyl-3-methylphenyl, N(C₂H₄CN)(C₄H₉) | 2-thienyl | CN | blue |

We claim:
1. A thienone compound of the formula

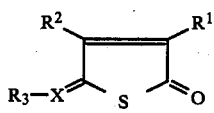

where
R¹ is cyano, C₁–C₄-alkoxycarbonyl, carbamoyl or C₁–C₄-monoalkylcarbamoyl or -dialkylcarbamoyl,
R² is hydrogen, C₁–C₈-alkyl, unsubstituted phenyl or phenyl substituted with C₁–C₄-alkyl, C₁–C₄-alkoxy, chlorine, bromine or nitro, furyl, thienyl or halogen,
X is nitrogen or CR⁴ where R⁴ is hydrogen, C₁–C₄-alkyl, C₁–C₄-alkoxycarbonyl, cyano or unsubstituted phenyl or phenyl substituted with C₁–C₄-alkyl, C₁–C₄-alkoxy, chlorine, bromine or nitro, and
R³ is a radical of the formula

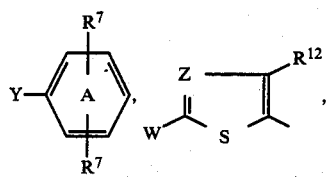

-continued (indole, styryl, indoline, isoindole structures)

where the ring A is phenyl or naphthyl,
Y is NR⁵R⁶ or OR⁸ where R⁵ and R⁶ are identical or different and each is independently of the other hydrogen, C₁–C₈-alkyl which is unsubstituted or substituted by hydroxyl, chlorine, cyano, C₁–C₄-alkoxy, C₁–C₄-alkanoyloxy, C₁–C₄-alkoxycarbonyloxy or phenyl, allyl, C₅–C₇-cycloalkyl or phenyl or together with the nitrogen atom joining them are a 5- or 6-membered saturated heterocyclic ring selected from the group consisting of pyrrolidino, piperidino, morpholino, piperazino and N-(C₁–C₄-alkyl) piperazino and R⁸ is C₁–C₄-alkyl or phenyl,
the R⁷s are independently of one another hydrogen, chlorine, bromine, hydroxyl, C₁–C₄-alkyl, C₁–C₄-alkoxy, unsubstituted or chlorine-, C₁–C₄-alkoxy- or phenoxy-substituted C₁–C₄-alkanoylamino, benzoylamino, $C_1$–$C_4$-mono- or -dialkylaminosulfonylamino, $C_1$–$C_4$-alkanoyloxy or phenylsulfonyloxy, $R^9$ is hydrogen, $C_1$–$C_4$-dialkylamino or $C_1$–$C_4$-alkoxy, $R^{10}$ is hydrogen or cyano, $R^{11}$ is hydrogen, chlorine, bromine or $C_1$–$C_4$-alkyl, $R^{12}$ is hydrogen, chlorine, bromine, $C_1$–$C_8$-alkyl, unsubstituted phenyl or phenyl substituted with $C_1$–$C_4$-alkyl, $C_1$–$C_4$-alkoxy, chlorine, bromine or nitro, or thienyl, W is $NR^5R^6$ or

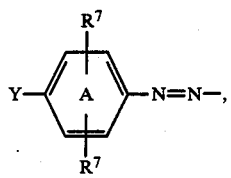

where $R^5$, $R^6$, $R^7$, Y and the ring A are each as defined above,

Z is nitrogen or $CR^1$ where $R^1$ is as defined above and n is 1, 2, 3 or 4 with the proviso that if $R^1$ is cyano, X is CH and $R^3$ is 4-dimethylaminophenyl or styryl, then $R^2$ is not methyl or phenyl and that if $R^1$ is cyano, X is CH and $R^3$ is phenyl or 4-methoxyphenyl, then $R^2$ is not phenyl.

2. A thienone compound as claimed in claim 1, wherein $R^1$ is cyano or carbamoyl, $R^2$ is $C_1$–$C_4$-alkyl, unsubstituted or methyl-, ethyl-, methoxy-, ethoxy-, chlorine- or bromine-substituted phenyl or thienyl, X is nitrogen or $CR^4$ where $R^4$ is hydrogen or cyano, and $R^3$ is a radical of the formula

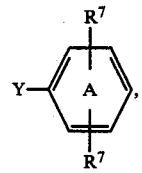

3. A thienone compound as claimed in claim 1, wherein $R^1$ is cyano, $R^2$ is methyl, unsubstituted or methoxy-substituted phenyl or thienyl, X is nitrogen or $CR^4$ where $R^4$ is hydrogen or cyano, and $R^3$ is a radical of the formula

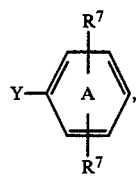

where the ring A is phenyl.

4. A method of dyeing fibers comprising applying a thienone compound of the formula

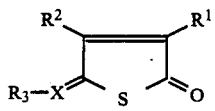

where $R^1$ is cyano, $C_1$–$C_4$-alkoxycarbonyl, carbamoyl or $C_1$–$C_4$-monoalkylcarbamoyl or -dialkylcarbamoyl, $R^2$ is hydrogen, $C_1$–$C_8$-alkyl, unsubstituted phenyl or phenyl substituted with $C_1$–$C_4$-alkyl, $C_1$–$C_4$-alkoxy, chlorine, bromine or nitro, furyl, thienyl or halogen, X is nitrogen or $CR^4$ where $R^4$ is hydrogen, $C_1$–$C_4$-alkyl, $C_1$–$C_4$-alkoxycarbonyl, cyano or unsubstituted phenyl or phenyl substituted with $C_1$–$C_4$-alkyl, $C_1$–$C_4$-alkoxy, chlorine, bromine or nitro, and $R^3$ is a radical of the formula

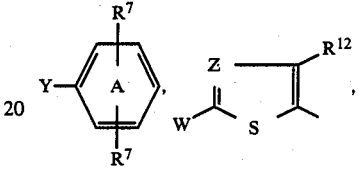

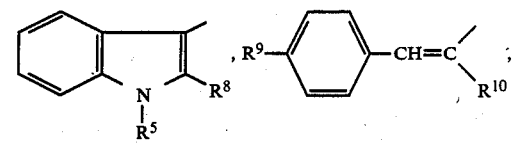

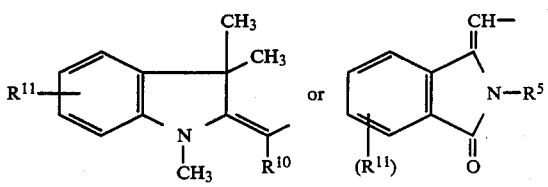

where the ring A is phenyl or naphthyl,

Y is $NR^5R^6$ or $OR^8$ where $R^5$ and $R^6$ are identical or different and each is independently of the other hydrogen, $C_1$–$C_8$-alkyl which is unsubstituted or substituted by hydroxyl, chlorine, cyano, $C_1$–$C_4$-alkoxy, $C_1$–$C_4$-alkanoyloxy, $C_1$–$C_4$-alkoxycarbonyloxy or phenyl, allyl, $C_5$–$C_7$-cycloalkyl or phenyl or together with the nitrogen atom joining them are a 5- or 6-membered saturated heterocyclic ring selected from the group consisting of pyrrolidino, piperidino, morpholino, piperazino and N-($C_1$–$C_4$-alkyl) piperazino and $R^8$ is $C_1$–$C_4$-alkyl or phenyl, the $R^7$s are independently of one another hydrogen, chlorine, bromine, hydroxyl, $C_1$–$C_4$-alkyl, $C_1$–$C_4$-alkoxy, unsubstituted or chlorine-, $C_1$–$C_4$-alkoxy- or phenoxy-substituted $C_1$–$C_4$-alkanoyl-amino, benzoylamino, $C_1$–$C_4$-mono- or -dialkylaminosulfonylamino, $C_1$–$C_4$-alkanoyloxy or phenylsulfonyloxy, $R^9$ is hydrogen, $C_1$–$C_4$-dialkylamino or $C_1$–$C_4$-alkoxy, $R^{10}$ is hydrogen or cyano, $R^{11}$ is hydrogen, chlorine, bromine or $C_1$–$C_4$-alkyl, $R^{12}$ is hydrogen, chlorine, bromine, $C_1$–$C_8$-alkyl, unsubstituted phenyl or phenyl substituted with $C_1$–$C_4$-alkyl, $C_1$–$C_4$-alkoxy, chlorine, bromine or nitro, or thienyl, W is $NR^5R^6$ or

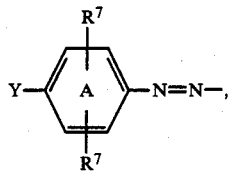
where $R^5$, $R^6$, $R^7$, Y and the ring A are each as defined above,
Z is nitrogen or $CR^1$ where $R^1$ is as defined above, and
n is 1, 2, 3 or 4.
* * * * *
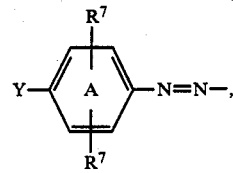
where $R^5$, $R^6$, $R^7$, Y and the ring A are each as defined above,
Z is nitrogen or $CR^1$ where $R^1$ is as defined above, and
n is 1, 2, 3 or 4.
* * * * *